(12) United States Patent
Horvath et al.

(10) Patent No.: US 7,619,171 B2
(45) Date of Patent: Nov. 17, 2009

(54) MULTIFUNCTION SURGICAL FOOTSWITCH

(75) Inventors: Christopher Horvath, Irvine, CA (US); Bruno Dacquay, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 570 days.

(21) Appl. No.: 11/474,668

(22) Filed: Jun. 26, 2006

(65) Prior Publication Data

US 2007/0043339 A1    Feb. 22, 2007

Related U.S. Application Data

(60) Provisional application No. 60/695,561, filed on Jun. 30, 2005.

(51) Int. Cl.
*H01H 3/14* (2006.01)

(52) U.S. Cl. .................. 200/86.5; 200/341

(58) Field of Classification Search ............. 200/61.85, 200/86.5, 334, 341–345; 307/112–120; 433/101; 74/512, 560–562
See application file for complete search history.

(56) References Cited

U.S. PATENT DOCUMENTS

| | | | |
|---|---|---|---|
| 4,837,857 A | 6/1989 | Scheller et al. | |
| 4,965,417 A | 10/1990 | Massie | |
| 4,983,901 A | 1/1991 | Lehmer | |
| 5,091,656 A | 2/1992 | Gahn | |
| 5,180,925 A * | 1/1993 | Lieb | 307/114 |
| 5,268,624 A | 12/1993 | Zanger | |
| 5,324,900 A * | 6/1994 | Gonser et al. | 200/86.5 |
| 5,554,894 A | 9/1996 | Sepielli | |
| 5,580,347 A | 12/1996 | Reimels | |
| 5,635,777 A | 6/1997 | Telymmonde et al. | |
| 5,787,760 A | 8/1998 | Thorlakson | |
| 6,039,565 A * | 3/2000 | Chou et al. | 433/29 |
| 6,179,829 B1 | 1/2001 | Bisch et al. | |
| 6,360,630 B2 * | 3/2002 | Holtorf | 74/512 |
| 6,452,123 B1 | 9/2002 | Chen | |
| 6,537,269 B1 | 3/2003 | Abe | |
| 6,689,975 B2 | 2/2004 | Metzler et al. | |
| 7,012,203 B2 * | 3/2006 | Hanson et al. | 200/86.5 |

(Continued)

FOREIGN PATENT DOCUMENTS

WO    WO 98/08442    3/1998

(Continued)

OTHER PUBLICATIONS

U.S. Appl. No. 60/667,290, filed Mar. 31, 2005, Horvath et al.

*Primary Examiner*—Michael A Friedhofer
*Assistant Examiner*—Lisa N Klaus
(74) *Attorney, Agent, or Firm*—Armando Pastrana, Jr.

(57) ABSTRACT

A multifunction surgical footswitch is disclosed, one embodiment of the surgical footswitch comprising: a base assembly, wherein the base assembly comprises a shroud and a heel plate; a stand-by/ready switch attached to the base assembly and operable to provide a stand-by/ready control signal to switch a laser between a stand-by and a ready state; and a firing switch attached to the base assembly and operable to provide a firing control signal to fire the laser. The surgical footswitch can further comprise an interface communicatively coupled to the firing switch and the stand-by/ready switch and operable to communicate the firing and the stand-by/ready control signals to the laser.

18 Claims, 2 Drawing Sheets

U.S. PATENT DOCUMENTS

| | | | |
|---|---|---|---|
| 7,019,234 B1 * | 3/2006 | Mezhinsky et al. | 200/86.5 |
| 7,084,364 B2 * | 8/2006 | Mezhinsky | 200/310 |
| 7,193,169 B2 * | 3/2007 | Mezhinsky et al. | 200/200 |
| 7,259,340 B2 * | 8/2007 | Blaha et al. | 200/310 |
| 7,323,646 B2 * | 1/2008 | Braaten | 200/18 |
| 7,381,917 B2 * | 6/2008 | Dacquay et al. | 200/86.5 |
| 7,422,432 B2 * | 9/2008 | Warner | 433/101 |
| 7,439,463 B2 * | 10/2008 | Brenner et al. | 200/86.5 |
| 2004/0115591 A1 | 6/2004 | Warner | |

FOREIGN PATENT DOCUMENTS

| | | |
|---|---|---|
| WO | WO 00/12037 | 3/2000 |
| WO | WO 02/01310 | 1/2002 |

* cited by examiner

MULTIFUNCTION SURGICAL FOOTSWITCH

CROSS-REFERENCE TO RELATED APPLICATIONS

This application claims priority under 35 U.S.C. §119 to U.S. Provisional Patent Application No. 60/695,561, filed Jun. 30, 2005, the entire contents of which are incorporated herein by reference.

TECHNICAL FIELD OF THE INVENTION

The present invention relates generally to surgical footswitches, and more particularly, to a multifunction surgical footswitch operable to provide a surgeon independent control of an ophthalmic laser surgical system.

BACKGROUND OF THE INVENTION

Footswitches are used with a variety of electrical and mechanical equipment and, in particular, have become an accepted part of the operator controls that enable the use of microsurgical and ophthalmic systems. Accordingly, the present footswitch invention will be described in terms of its use with microsurgical systems and, in particular, its use with ophthalmic laser surgical systems.

When surgically treating a patient, for example, during ophthalmic surgery, a surgeon may use a complex patient treatment apparatus/surgical system that may require the control of a variety of different pneumatic and electronically driven subsystems: Typically, the operation of these subsystems is controlled by a microprocessor-driven console. The microprocessor within the surgical console may receive mechanical inputs from either the surgeon/operator or from an assistant to the surgeon/operator. For example, an assistant may directly manipulate controls on the surgical console, while the surgeon/operator may use a control input device, such as a footswitch, to provide mechanical inputs. In the case of a footswitch, the mechanical inputs originate from the movement of the surgeon's foot to control the operation of a subsystem within the surgical system. The mechanical inputs are translated into electrical signals that are then fed to the microprocessor to control the operational characteristics of the desired subsystem. One example of such a subsystem is a laser system used in ophthalmic laser eye surgery, such as the EYELITE® photocoagulator manufactured by Alcon Laboratories, Inc. of Irvine, Calif.

Examples of footswitches designed for translating mechanical inputs into control signals for a complex patient treatment apparatus may be found in several U.S. Patents, including U.S. Pat. Nos. 4,837,857 (Scheller, et al.), 4,965,417 (Massie), 4,983,901 (Lehmer), 5,091,656 (Gahn), 5,268,624 (Zanger), 5,554,894 (Sepielli), 5,580,347 (Reimels), 5,635,777 (Telymonde, et al), 5,787,760 (Thorlakson), 5,983,749 (Holtorf), and 6,179,829 B1 (Bisch, et al), and in International Patent Application Publication Nos. WO 98/08442 (Bisch, et al.), WO 00/12037 (Chen), and WO 02/01310 (Chen). These patents and patent applications focus primarily on footswitches that include a foot pedal or tillable treadle similar to the accelerator pedal used to govern the speed of an automobile. The movement of the foot pedal or tillable treadle typically provides a linear control input. Such linear control inputs may be used, for example, for regulating vacuum, rotational speed, power, or reciprocal motion.

Certain footswitches, however, such as those used for ophthalmic laser surgery, may consist primarily of a casing having a switch operably connected to the laser surgical system. The switch is typically a single on/off type switch dedicated to firing a laser that has been previously placed in a "ready" condition. In a typical ophthalmic laser surgery, such as for photocoagulation, a laser subsystem is first prepared for the surgery by, for example, setting the proper parameters for the type of surgery, (e.g., power level, pulse duration, shot pattern, etc.) The laser is typically in a stand-by state (laser on, but incapable of being fired from the footswitch) when the laser system is powered on. For safety reasons, the user must take an affirmative step to place the laser in a "ready" condition from the stand-by state. A laser in the "ready" condition is configured to fire when the fire switch in the footswitch is actuated. Thus, there must be a conscious user decision to change the laser state from "stand-by" to "ready" by, for example, actuation of a button on the laser system console. Typically, a regulatory requirement imposes the additional restriction of a minimum two-second delay (internal to the console) between switching to the "ready" state and the laser actually entering the "ready" state.

To place a laser in a "ready" condition, typically a surgical assistant must manipulate a control at the control panel of the surgical subsystem; for example, the assistant may press a button that switches the laser from stand-by to ready. A surgical assistant typically performs this function because during a surgical procedure, at the point when the laser is needed, the surgeon is well into the surgery and not at a point where he/she may readily extricate from the surgical field to manipulate controls at the surgical console without disrupting the surgery. Further, in some instances the surgeon may be engaged in the surgical field and the assistant may also be otherwise engaged away from the control panel. A delay and inefficiency are imposed by requiring the assistant or the surgeon to move to the control panel to prepare the laser. A surgeon is thus typically dependent on a surgical assistant to perform this function for him or her.

Prior art systems do not provide a means by which a surgeon can, independently of an assistant, easily place a laser in a ready position and continue with the laser surgery without having to detract attention from the surgery. Instead, the surgeon must rely on an assistant. Once the laser is in a ready state, however, prior art systems do provide a firing switch in the laser system footswitch that the surgeon can actuate to fire the laser.

Therefore, a need exists for a multifunction surgical footswitch that can provide a surgeon the ability to independently operate a laser of an ophthalmic laser surgical system while maintaining his/her attention within a surgical field.

BRIEF SUMMARY OF THE INVENTION

The embodiments of the multifunction surgical footswitch of the present invention substantially meet these needs and others. Embodiments of the present invention can comprise a switching mechanism within a footswitch assembly that duplicates or replaces the prior art laser firing and stand-by-to-ready laser state switching functionality of the controls on a footswitch and surgical console. One embodiment of the multifunction surgical footswitch of this invention is a surgical footswitch comprising: a base assembly, wherein the base assembly comprises a shroud and a heel plate; a stand-by/ready switch attached to the base assembly and operable to provide a stand-by/ready control signal to switch a laser between a stand-by and a ready state; and a firing switch attached to the base assembly and operable to provide a firing control signal to fire the laser. The surgical footswitch can further comprise an interface communicatively coupled to the firing switch and the stand-by/ready switch and operable to communicate the firing and the stand-by/ready control signals to the laser. The laser can be operably coupled to a surgical console operable to control the laser, and the interface can be operable to communicatively couple the surgical footswitch to the surgical console and to communicate the firing and the stand-by/ready control signals to the surgical console. The surgical console can be operable to control the laser based on the firing and the stand-by/ready control signals.

The stand-by/ready switch can be attached to an inner surface of the shroud and positioned so that it can be actuated by an operator's foot, such as by an upward movement of the operator's foot. The heel plate is constructed and arranged so as to be beneath the operator's heel and operable to keep the base assembly in contact with a surface beneath the base assembly (e.g., a floor) in response to downward pressure from the operator's heel. The surgical footswitch can further comprise a lift sensor assembly operable to detect lifting of the base assembly from the surface and to deactivate the stand-by/ready switch based on the detected lifting. The lift sensor assembly can be an ultrasound proximity sensor, an optical sensor, a radio frequency signal modulation sensor, a radar sensor, and an accelerometer, or any other such sensor known to those having skill in the art and operable to detect the lifting of the surgical footswitch.

Embodiments of the surgical footswitch of this invention can also comprise a foot sensor assembly operable to detect the presence of an operator's foot and to generate a control signal in response to the detected foot presence. The control signal can be transmitted to the surgical console where it can be operable, for example, to cause the laser to warm-up in preparation for firing. Embodiments of the present invention can comprise a wired or wireless interface to communicate control signals between the surgical footswitch and the surgical console, and can include additional switches attached to the base assembly operable to produce additional control signals operable to control one or more additional functions at the surgical console. Other embodiments of the present invention can include an ophthalmic surgical system comprising a surgical footswitch in accordance with the teachings of this invention and a laser with or without a surgical console. Embodiments of the present invention can further include a surgical footswitch having a progressively actuated firing switch/laser firing sequence and a method for switching a laser between a stand-by and a ready condition in accordance with the teachings of the present invention.

Embodiments of the present invention can be implemented within any ophthalmic surgical system as known to those in the art, and in particular, in the EyeLite® Laser Surgical System manufactured by Alcon Manufacturing, Ltd. of Irvine, Calif. The embodiments of this invention can be incorporated within any such surgical machine or system for use in ophthalmic or other surgery. Other uses for a multifunction surgical footswitch designed in accordance with the teachings of this invention will be known to those familiar with the art and are contemplated to be within the scope of this invention.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings in which like reference numerals indicate like features and wherein.

DETAILED DESCRIPTION OF THE INVENTION

Figure 1:
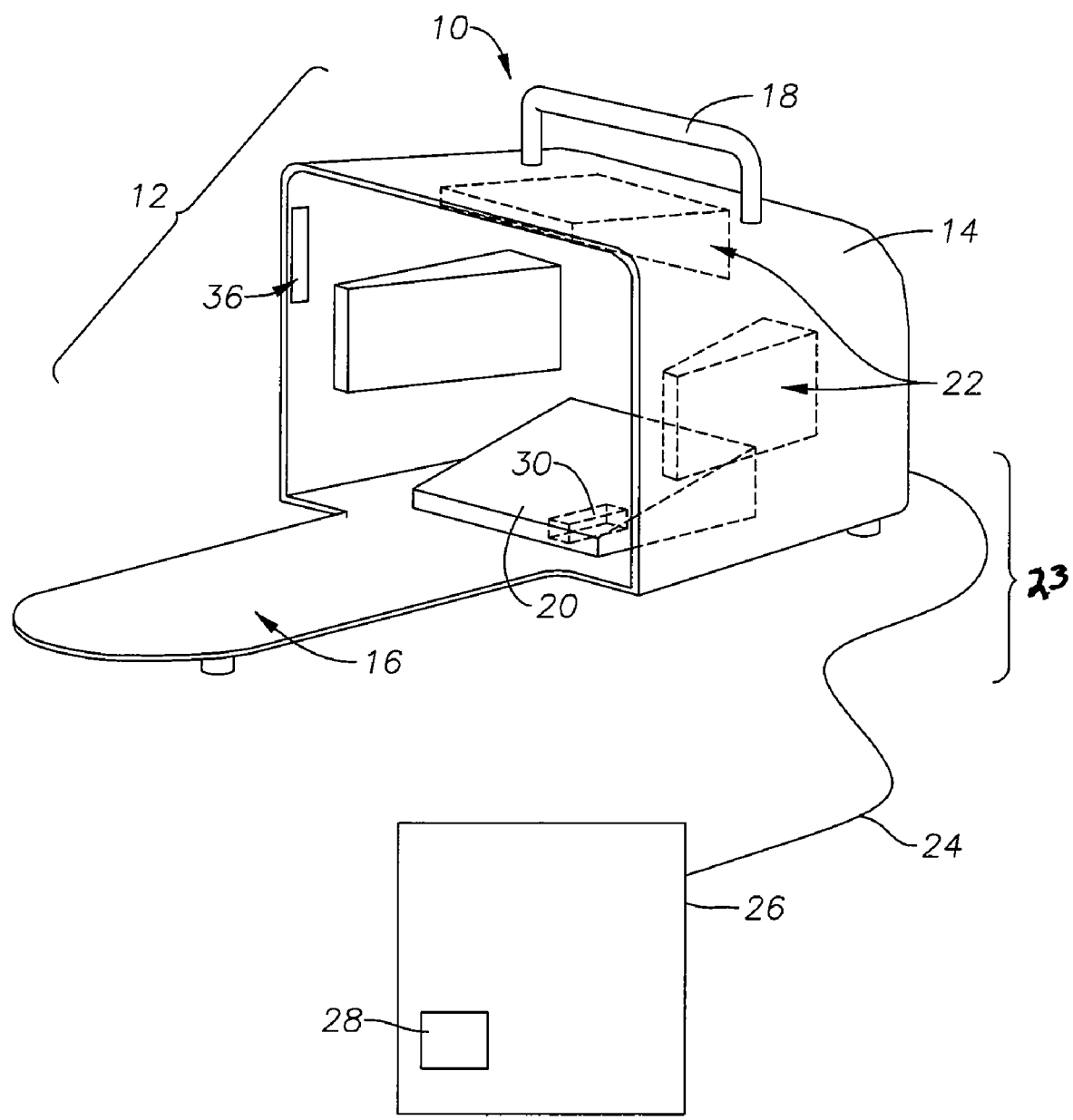
FIG. 1 illustrates an embodiment of a footswitch assembly according to the teachings of this invention.

Preferred embodiments of the present invention are illustrated in the FIGUREs like numerals being used to refer to like and corresponding parts of the various drawings.

The various embodiments of the present invention provide a multifunction surgical footswitch that allows a surgeon to both place a surgical laser in a ready condition and fire the laser once it is in the ready condition. Embodiments can comprise a multi-position switch or multiple switches for controlling various functions.

In the prior art, footswitches for the operation of surgical lasers typically comprise a shroud to prevent inadvertent or accidental firing of a laser in the ready position. One embodiment of the multifunction surgical footswitch of this invention takes advantage of the shroud for positioning a switch such that it is attached to an inner surface of the shroud above a user's foot. The user can then actuate the switch using an upward motion of his or her foot. Other embodiments can instead have this laser "stand-by/ready" switch placed on a side wall of the shroud such that a side motion of the surgeon's foot can actuate the switch. Other positions as may be required, or that may be useful, for a particular implementation, are contemplated to be within the scope of this invention.

During a laser surgery, a surgeon is routinely required to position himself or herself in various different positions relative to a patient's eye, requiring the surgeon to move around the patient. Consequently, the footswitch for firing the laser is also routinely moved around during a surgery. Surgeon's have also become accustomed to using the footswitch shroud as a convenient means to pick-up and move the footswitch (e.g., by using the shroud as a sort of slipper). Because of this, a switch operable to place a laser in a ready condition from a stand-by condition and that is positioned above the surgeon's foot inside the shroud will be actuated each time the surgeon lifts the footswitch. Undesired switching of the laser from standby to ready, and vice-versa, can thus occur with such a design.

Embodiments of the present invention can prevent such undesired switching by incorporating sensors into the footswitch assembly to detect the footswitch being lifted off the ground when being repositioned. Embodiments of this invention can thus differentiate between a switch actuation due to repositioning the footswitch and a switch actuation to affirmatively switch a laser from a stand-by to a ready condition or vice-versa. Lifting sensors incorporated into an embodiment of the present invention to detect such movement can comprise, for example, accelerometers, button switches on the bottom of the footswitch, ultrasound proximity sensors, optical sensors, a radio frequency signal modulation sensor, a radar sensor or any other such sensor known to those having skill in the art and operable to detect lifting of the surgical footswitch. Embodiments can also comprise sensors (e.g., positioned along the shroud) that can detect, for example, insertion of the surgeon's foot into the shroud in preparation for use. The sensors can then cause control signals to be generated, for example, that are operable to cause the laser to warm up in preparation for use. In this way, laser reliability can be increased while also decreasing lag times during the surgery.

Embodiments of the present invention can thus reduce a surgeon's dependence on his/her assistant during laser eye surgery and make the surgery flow more efficient by allowing the surgeon to independently control the stand-by/ready condition of the laser, and fire the laser, from a single multifunction surgical footswitch. A dedicated mode switch on the laser console can be retained for redundancy, but need not be the only means for making the laser ready. The surgeon will therefore not need to use his or her hands or rely on an assistant to transition the laser from stand-by to ready, and vice versa, during a surgery, freeing the surgeon to dedicate his or her attention to the surgical field.

FIG. 1 shows an embodiment of a footswitch assembly 10 according to this invention. The footswitch assembly 10 includes a body or housing 12 that comprises a shroud 14 and a heel plate 16. Shroud 14 and heel plate 16 can be a single integrated assembly or separate units coupled together to form housing 12. All of these components can be made from any suitable material, such as stainless steel, titanium, or plastic. Embodiments may include a handle 18 that can be attached to housing 12. Attached inside shroud 14 are a first (laser stand-by/ready) switch 22 and a second (laser firing) switch 20. Laser firing switch 20 is typically positioned forward of and on or near the same plane as heel plate 16, such that a surgeon inserting his or her foot into shroud 14 can press down on laser switch 20 while placing his or her heel on some portion of heel plate 16. In the embodiment of the multifunction surgical footswitch of this invention illustrated in FIG. 1, laser stand-by/ready switch 22 can be attached inside shroud 14 such that it is positioned above the ball/toes of a surgeon's foot and can be actuated by an upward motion of the surgeon's foot. When actuating a stand-by/ready switch 22 positioned this way, housing 12 is maintained on a surface, such as a floor, by the pressure of a surgeon's heel pressing down on heel plate 16.

Laser firing switch 20 is typically a press and hold type switch that can fire a single shot of varying duration or multiple shots, depending on the surgeon's configurable laser setting. Laser stand-by/ready switch 22 is typically a single action button switch that can switch the laser mode from stand-by to ready (or vice-versa) upon pressing and release. However, either switch can be any other type switch as known to those having skill in the art that can perform the functions described herein.

Footswitch assembly 10 can also include an interface 23, comprising one or more cable assemblies 24, to operably couple the footswitch assembly 10 to a surgical console 26/laser 28 and operable to communicate control signals from footswitch assembly 10 to console 26/laser 28. Surgical console 26 is operable to control laser 28, for example, to cause laser 28 to switch modes and/or to fire based on the control signals that are relayed from the footswitch assembly 10 to the surgical console 26. Surgical console 26 includes for purposes of this invention, the control and/or processing circuitry for laser 28, whether surgical console 26 is a separate enclosure or the same enclosure as that of laser 28. Surgical console 26 can be any console housing laser 28, including, for example, a multi-purpose console, such as a vitreo-retinal surgical console that includes laser 28, or a dedicated laser 28 enclosure.

Figure 2:
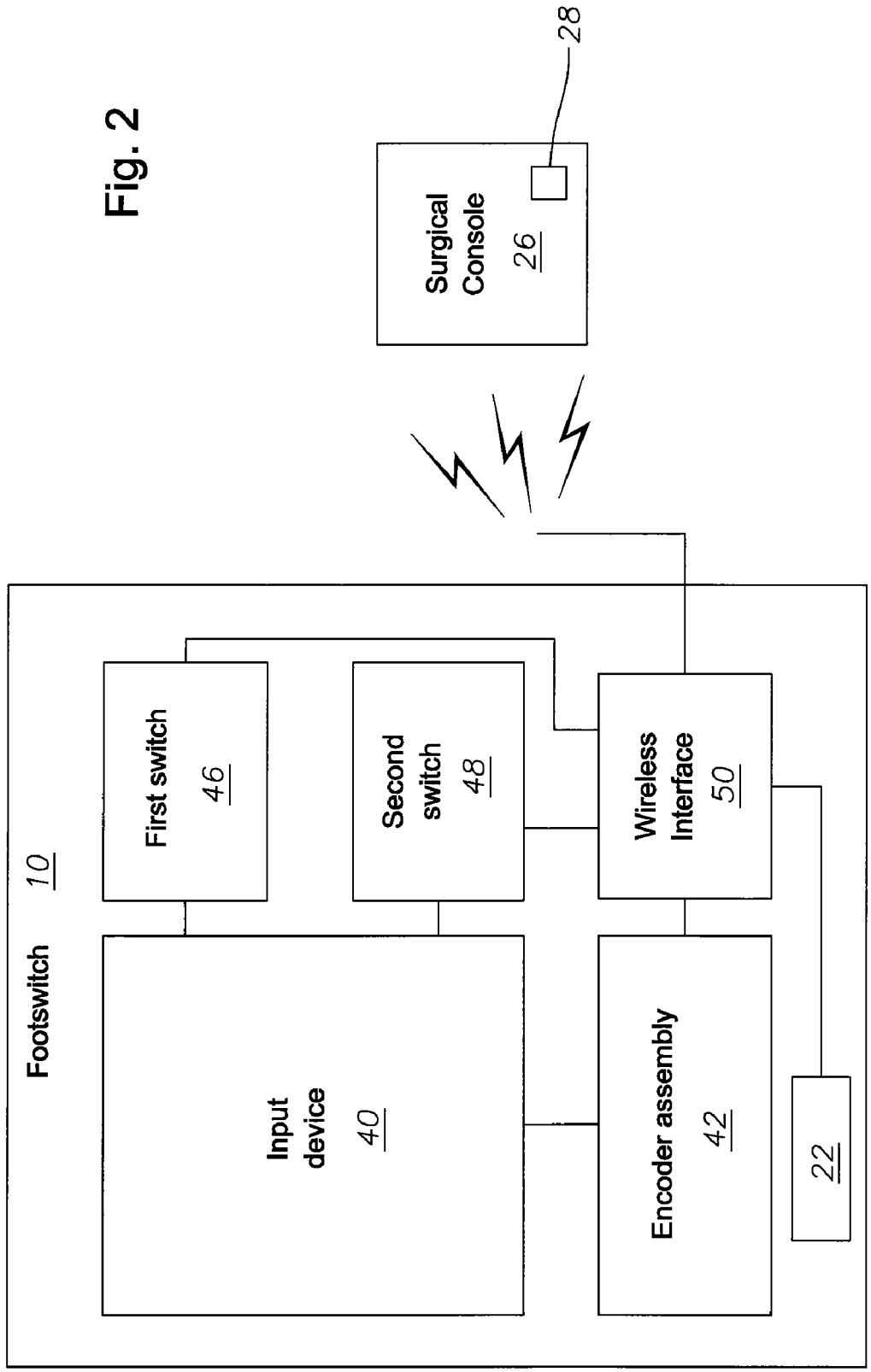
FIG. 2 is a functional diagram of an embodiment of the multifunction surgical footswitch of this invention having a wireless interface.

Another embodiment of footswitch assembly 10 can comprise a wireless interface 50, as shown in FIG. 2, that is operable to establish a wireless communication pathway between footswitch assembly 10 and surgical console 26 to accomplish the same control signal transmission in a wireless manner. A wireless footswitch is disclosed in related U.S. patent application 60/667,290 filed Mar. 31, 2005, the entire contents of which are incorporated herein by reference. Surgical console 26 and laser 28 can be, for example, an EYE-LITE® photocoagulator manufactured by Alcon Laboratories, Inc. of Irvine, Calif.

The embodiment of FIG. 1 shows laser stand-by/ready switch 22 attached inside shroud 14 and positioned above where the ball of a surgeon's foot will normally be when footswitch assembly 10 is in use. However, stand-by/ready switch 22 can be also positioned, for example, on an inner side of shroud 14, or next to laser firing switch 20 on the base of housing 12. The position of stand-by ready switch 22 can be changed to accommodate a given implementation. Further, embodiments of the footswitch assembly 10 can comprise one or more additional switches attached to footswitch assembly 10 and each operable to provide a control signal operable to control a function at surgical console 26 (e.g., adjust laser power, pulse duration, etc.).

Typically, the stand-by/ready transition of the laser 28 is initiated when the stand-by/ready switch 22 is released, not when it is engaged. One embodiment of the footswitch of this invention can comprise a stand-by/ready switch 22 of this type together with a lifting sensor assembly 30 placed, for example, on or beneath the footswitch assembly 10 and operable to detect lifting of footswitch assembly 10. Such an embodiment can provide the ability to distinguish between a surgeon engaging stand-by/ready switch 22 to change the laser's status, and a surgeon lifting footswitch assembly 10 to move it around (for example, when using footswitch assembly 10 with the Alcon LIO System manufactured by Alcon Laboratories, Inc. of Irvine, Calif.).

In an embodiment of the present invention incorporating a lifting sensor assembly 30, when a surgeon lifts footswitch assembly 10 to move it, although he or she will engage stand-by/ready switch 22, the lifting sensor assembly 30 will detect the lifting of footswitch assembly 10 from its supporting surface. Lifting sensor assembly 30 is operable to prevent the actuation (release) of stand-by/ready switch 22 from causing laser 28 to change modes when lifting sensor assembly 30 detects lifting of footswitch assembly 10 from a supporting surface, such as a floor. Thus, after a surgeon lifts, moves and returns footswitch assembly 10 to the supporting surface, stand-by/ready switch 22 will be released, but the release (actuation) of switch 22 will not result in a stand-by/ready transition of laser 28. Lifting sensor assembly 30 will not prevent a desired switching of the laser 28 stand-by/ready condition during normal operation because the pressure of the surgeon's heel on heel plate 16 will prevent lifting of footswitch assembly 10. Lifting sensor assembly 30 can comprise accelerometers, button switches on the bottom of the footswitch, pressure sensors, ultrasound proximity sensors, optical sensors, a radio frequency signal modulation sensor, a radar sensor or any other such sensor known to those having skill in the art and operable to detect lifting of the surgical footswitch.

Another embodiment of the present invention can incorporate sensors, such as a foot sensor assembly 36, into, for example, shroud 14 of housing 12 to detect the presence of a surgeon's foot within the shroud 14. Foot sensor assembly 36 can be operable to detect the surgeon's foot and to provide a control signal to console 26 operable, for example, to warm up laser 28 or otherwise prepare the laser surgical system for firing. Foot sensor assembly 36 can comprise, for example, ultrasound proximity sensors, a mechanical switch gate (e.g., a shroud entry door), an optical light gate (e.g., LED photodiode or laser photodiodes), radio frequency ("RF") signal modulation sensors, radar sensor, accelerometers, an optical sensor or any such sensor operable to sense such movement as will be known to those having skill in the art. Embodiments of the footswitch of this invention can comprise any combination of such lift and/or foot presence sensors.

FIG. 2 is a functional diagram of an embodiment of the multifunction surgical footswitch of this invention incorporating a wireless interface 50 for communicating control signals for the various functions of the present invention. In this embodiment, surgical footswitch assembly 10 includes an input device 40, which can be, for example, a pedal, an encoder assembly 42 and a wireless interface 50. This embodiment also comprises two switches, a first switch 46 and a second switch 48, that operably couple to the mechanical input device 40. Encoder 42 is operable to encode the control signals to be transmitted by wireless interface 50 to surgical console 26. An embodiment of this invention can also comprise the operably coupled first switch 46, second switch 48 and mechanical input device 40 with a wired interface, such as wireless interface 13 of FIG. 1.

The embodiment of FIG. 2 is a wireless embodiment of surgical footswitch 10 of this invention having a progressive laser firing sequence. However, a wired embodiment having a progressive laser firing sequence as described below is also contemplated to be within the scope of this invention. Input device 40 is analogous to the laser firing switch 20 of FIG. 1 in its laser firing function, but has a progressive actuation functionality as described below. Further, as in the other embodiments of the present invention, the embodiment of FIG. 2 can also include a combination of switches and functions as described herein, and in particular the stand-by/ready switching functionality of the present invention. Input device 40 can be a pedal, other mechanical input device, or any other such device that can provide the progressive action as described herein and that will be familiar to those having skill in the art.

In operation, first switch 46 is actuated and generates a first control signal as input device 40 orients past a first determined point. The first control signal is operable, for example, to initialize surgical laser 28 within the surgical system. The first switch 46 may be activated, for example, when the input device 40 is initially depressed. The second switch 48 produces a second control signal offset in time from the first control signal produced by the activation of first switch 46. For example, second switch 48 may be activated as pedal 40 nears the end of its angular range of motion (i.e., when the pedal 40 is fully depressed). The second control signal may direct the firing of surgical laser 28.

The trigger time between the activation of first switch 46 and second switch 48 may allow, for example, the stress on the laser 28 to be reduced. In such an implementation, the trigger time between the activation of the first switch 46 and the second switch 48 allows the laser 28 to slowly warm up before firing. Note that the functionality of first switch 46 and second switch 48 can be incorporated within a single laser firing switch 20 described with reference to FIG. 1. For example, referring back to FIG. 1, stand-by/ready switch 22 may be depressed and released to place the laser 28 in a ready condition from a stand-by condition. Then, laser firing switch 20, which can incorporate in one embodiment the functions of first switch 46 and second switch 48, ramps the laser 28 up to firing and then fires the laser 28 in the continuous movement of the surgeon's foot from initially depressing input device 40 (actuating first switch 46) to fully depressing input device 40 (actuating second switch 48).

In such an embodiment, laser firing switch 20 can comprise a pedal, such as pedal 40, operably coupled to a multi-position switch or switches having the functionality of first switch 46 and second switch 48. In one embodiment, the trigger time between the activation of the two switches 46 and 48 can be between about 100 ms and 300 ms. The actual time may depend on the foot speed of the operator. This allows laser 28 to be slowly ramped to power over the span of about 100 ms to about 300 ms (note that this is after the laser has already been placed in a ready condition from a stand-by condition). This is particularly useful for certain lasers, known to those having skill in the art, that can not be turned on in less than 50 ms. The reduced stress associated with firing the laser in accordance with this embodiment of the present invention will result in improved laser performance and reliability. Although footswitch assembly 10 is illustrated in the embodiment of FIG. 2 as establishing a wireless communication pathway between the footswitch assembly 10 and surgical laser 28, footswitch assembly 10 may instead be physically coupled to the control circuits associated with initializing and firing laser 28, such as by a cable assembly 24 of FIG. 1.

The present invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims. As may be used herein, the terms "substantially" and "approximately" provide an industry-accepted tolerance for their corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" include direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output(s), etc., to perform one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

While the present invention has been described with reference to the general area of laser ophthalmic surgery, the teachings contained herein can apply equally to any surgical system where it is desirous to control a laser subsystem.

What is claimed is:

1. A surgical footswitch, comprising:
   a base assembly, wherein the base assembly comprises a shroud and a heel plate;

a stand-by/ready switch attached to the base assembly and operable to produce a stand-by/ready control signal to switch a laser between a stand-by and a ready state;

a firing switch attached to the base assembly and operable to produce a firing control signal to fire the laser; and an interface communicatively coupled to the firing switch and the stand-by/ready switch and operable to communicate the firing control signal and the stand-by/ready control signal to the laser.

2. The surgical footswitch of claim 1, wherein the laser is operably coupled to a surgical console operable to control the laser, and wherein the interface is operable to communicatively couple the surgical footswitch to the surgical console and to communicate the firing control signal and the stand-by/ready control signal to the surgical console, wherein the surgical console is operable to control the laser based on the firing control signal and the stand-by/ready control signal.

3. The surgical footswitch of claim 2, wherein the control signal is transmitted to the surgical console and is operable to cause the laser to warm-up in preparation for firing.

4. The surgical footswitch of claim 1, wherein the stand-by/ready switch is attached to an inner surface of the shroud.

5. The surgical footswitch of claim 4, wherein the stand-by/ready switch is positioned above the operator's foot, and wherein the heel plate is constructed and arranged so as to be beneath the operator's heel and operable to keep the base assembly in contact with a surface beneath the base assembly in response to downward pressure from the operator's heel.

6. The surgical footswitch of claim 5, further comprising a lift sensor assembly operable to detect lifting of the base assembly from the surface and to deactivate the stand-by/ready switch based on the detected lifting.

7. The surgical footswitch of claim 6, wherein the lift sensor assembly is selected from the group consisting of an ultrasound proximity sensor, an optical sensor, a radio frequency signal modulation sensor, a radar sensor, a pressure sensor and an accelerometer.

8. The surgical footswitch of claim 1, further comprising a foot sensor assembly operable to detect the presence of an operator's foot and to generate a control signal in response to the detected foot presence.

9. The surgical footswitch of claim 8, wherein the foot sensor assembly is selected from the group consisting of an ultrasound proximity sensor, an optical sensor, a radio frequency signal modulation sensor, a radar sensor, a mechanical switch gate, an optical light gate and an accelerometer.

10. The surgical footswitch of claim 1, wherein the interface is a wireless interface.

11. The surgical footswitch of claim 1, wherein the interface comprises a cable assembly.

12. The surgical footswitch of claim 1, further comprising one or more additional switches operable to provide one or more additional control signals operable to control one or more laser functions.

13. The surgical footswitch of claim 12, wherein the one or more functions comprise laser power and pulse duration.

14. The surgical footswitch of claim 1, wherein the shroud and the heel plate are an integrated assembly.

15. The surgical footswitch of claim 1, wherein the laser is an ophthalmic surgical laser.

16. A surgical footswitch, comprising:

a base assembly, wherein the base assembly comprises a shroud and a heel plate;

a stand-by/ready switch attached to the base assembly and operable to produce a stand-by/ready control signal to switch a laser between a stand-by and a ready state;

a firing switch attached to the base assembly and operable to produce a firing control signal to fire the laser; and an interface communicatively coupled to the firing switch and to the stand-by/ready switch and operable to communicatively couple the surgical footswitch to a surgical console and to communicate the firing control signal and the stand-by/ready control signal to the surgical console, wherein the surgical console is operable to control the laser based on the firing control signal and the stand-by/ready control signal.

17. A surgical footswitch, comprising:

a base assembly, wherein the base assembly comprises a shroud and a heel plate;

a stand-by/ready switch attached to the base assembly and operable to produce a stand-by/ready control signal to switch a laser between a stand-by and a ready state;

a firing switch attached to the base assembly and operable to produce a firing control signal to fire the laser; and an interface communicatively coupled to the firing switch and to the stand-by/ready switch and operable to communicate the firing control signal and the stand-by/ready control signal to the laser.

18. An ophthalmic surgical system, comprising:

a surgical console;

a laser; and a surgical footswitch, wherein the surgical footswitch comprises:

a base assembly, wherein the base assembly comprises a shroud and a heel plate;

a stand-by/ready switch attached to the base assembly and operable to produce a stand-by/ready control signal to switch a laser between a stand-by and a ready state;

a firing switch attached to the base assembly and operable to produce a firing control signal to fire the laser; and an interface communicatively coupled to the firing switch and to the stand-by/ready switch and operable to communicatively couple the surgical footswitch to a surgical console and to communicate the firing control signal and the stand-by/ready control signal to the surgical console, wherein the surgical console is operable to control the laser based on the firing control signal and the stand-by/ready control signal.

* * * * *

UNITED STATES PATENT AND TRADEMARK OFFICE
CERTIFICATE OF CORRECTION

PATENT NO. : 7,619,171 B2  Page 1 of 1
APPLICATION NO. : 11/474668
DATED : November 17, 2009
INVENTOR(S) : Horvath et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this

Twenty-sixth Day of October, 2010

David J. Kappos
*Director of the United States Patent and Trademark Office*